(12) United States Patent
Shannon, Jr.

(10) Patent No.: US 6,193,716 B1
(45) Date of Patent: Feb. 27, 2001

(54) ELECTROSURGICAL DEVICE FOR UVULOPALATOPLASTY

(76) Inventor: Malcolm L. Shannon, Jr., 6199 S. Jamaica Ct., Englewood, CO (US) 80111

( * ) Notice: Subject to any disclaimer, the term of this patent is extended or adjusted under 35 U.S.C. 154(b) by 0 days.

(21) Appl. No.: 09/348,146

(22) Filed: Jul. 6, 1999

Related U.S. Application Data

(63) Continuation of application No. 08/854,926, filed on May 13, 1997, now Pat. No. 5,921,983.

(51) Int. Cl.[7] .................................................. A61B 18/18
(52) U.S. Cl. .................................. 606/45; 606/48; 606/50
(58) Field of Search ........................... 606/39–42, 45–52; 128/898

(56) References Cited

U.S. PATENT DOCUMENTS

| | | |
|---|---|---|
| 373,399 | 11/1887 | Hamilton . |
| D. 401,350 | 11/1998 | Shannon, Jr. . |
| 1,798,902 | 3/1931 | Raney . |
| 1,881,250 | 10/1932 | Tomlinson . |
| 1,978,495 | 10/1934 | Landau . |
| 3,920,021 | 11/1975 | Hiltebrandt . |
| 4,060,087 | 11/1977 | Hiltebrandt et al. . |
| 4,198,957 | 4/1980 | Cage et al. . |
| 4,353,371 | 10/1982 | Cosman . |
| 4,418,692 | 12/1983 | Guay . |
| 4,719,914 | 1/1988 | Johnson . |
| 4,811,733 | 3/1989 | Borsanyi et al. . |
| 4,911,159 | 3/1990 | Johnson et al. . |
| 4,985,030 | * 1/1991 | Melzer et al. ............................ 606/51 |
| 5,085,659 | 2/1992 | Rydell . |
| 5,197,964 | 3/1993 | Parins . |
| 5,290,286 | 3/1994 | Parins . |
| 5,366,476 | * 11/1994 | Noda ....................................... 606/206 |

* cited by examiner

Primary Examiner—Linda C. M. Dvorak
Assistant Examiner—Roy Gibson
(74) Attorney, Agent, or Firm—Dorr, Carson, Sloan & Birney, P.C.

(57) ABSTRACT

An electrosurgical device for performing uvulopalatoplasty is provided. The device of the present invention includes two configurations. The first configuration includes a handle having an actuator mechanism which actuates a barrel fixedly mounted to a handle. This embodiment is contemplated to be disposable for single patient use. The second configuration includes a handle having an actuator mechanism having a detachable barrel. Both devices of the present invention are designed to fit easily into a patient's mouth and maximize the surgeon's manual control.

16 Claims, 7 Drawing Sheets

CONTINUED RESHAPING BY REMOVING PORTION OF UVULA

RESHAPING PALATE WITH VERTICAL INCISIONS

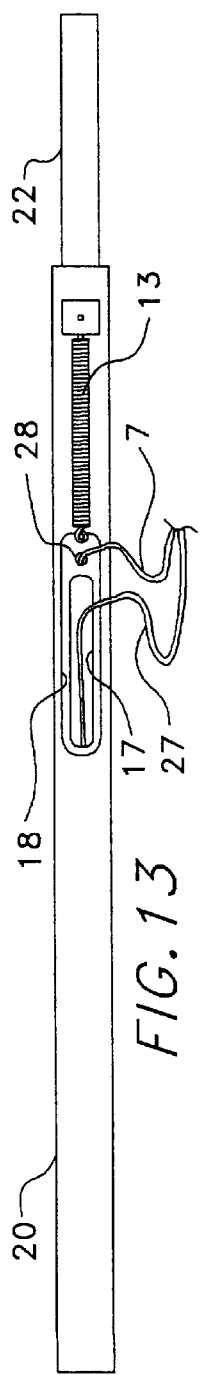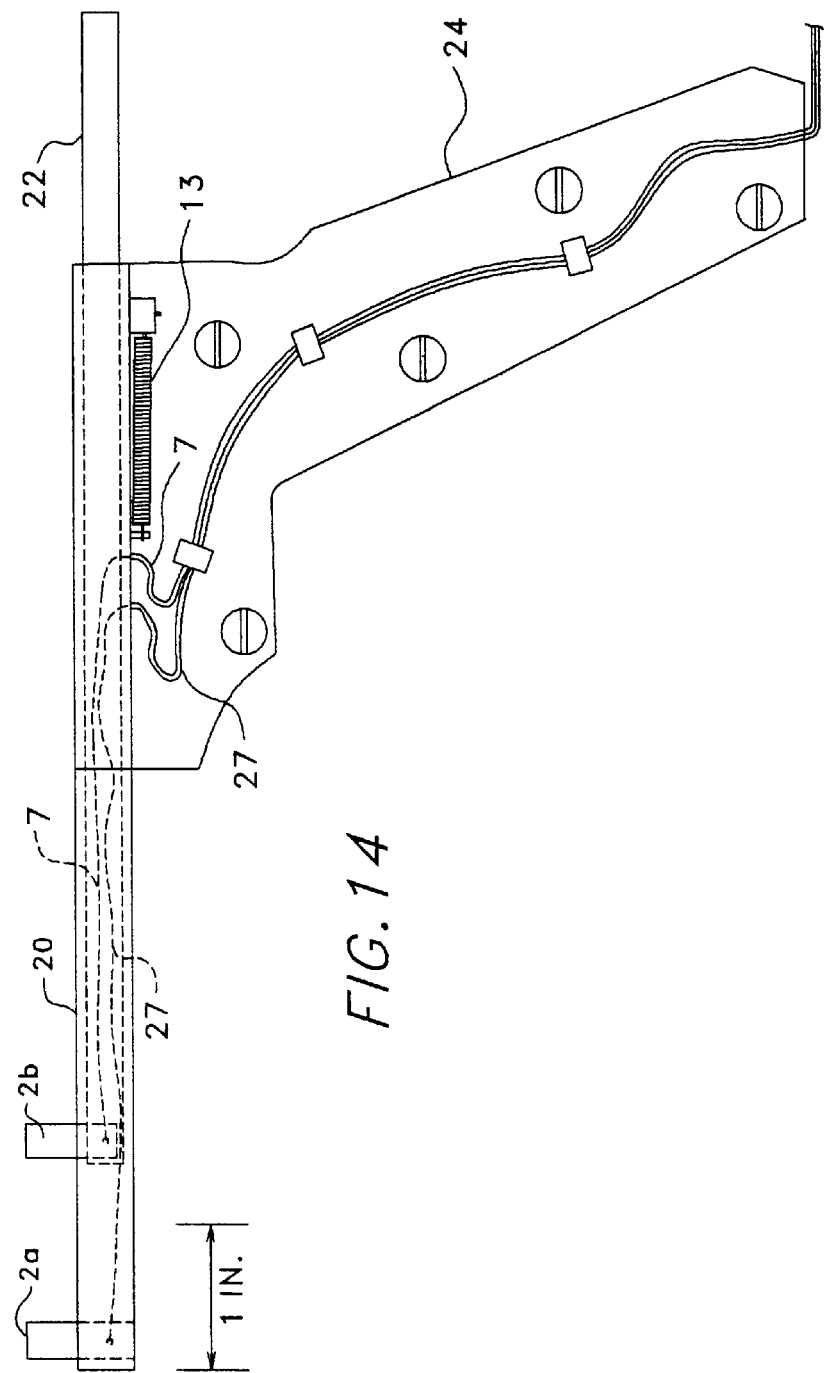

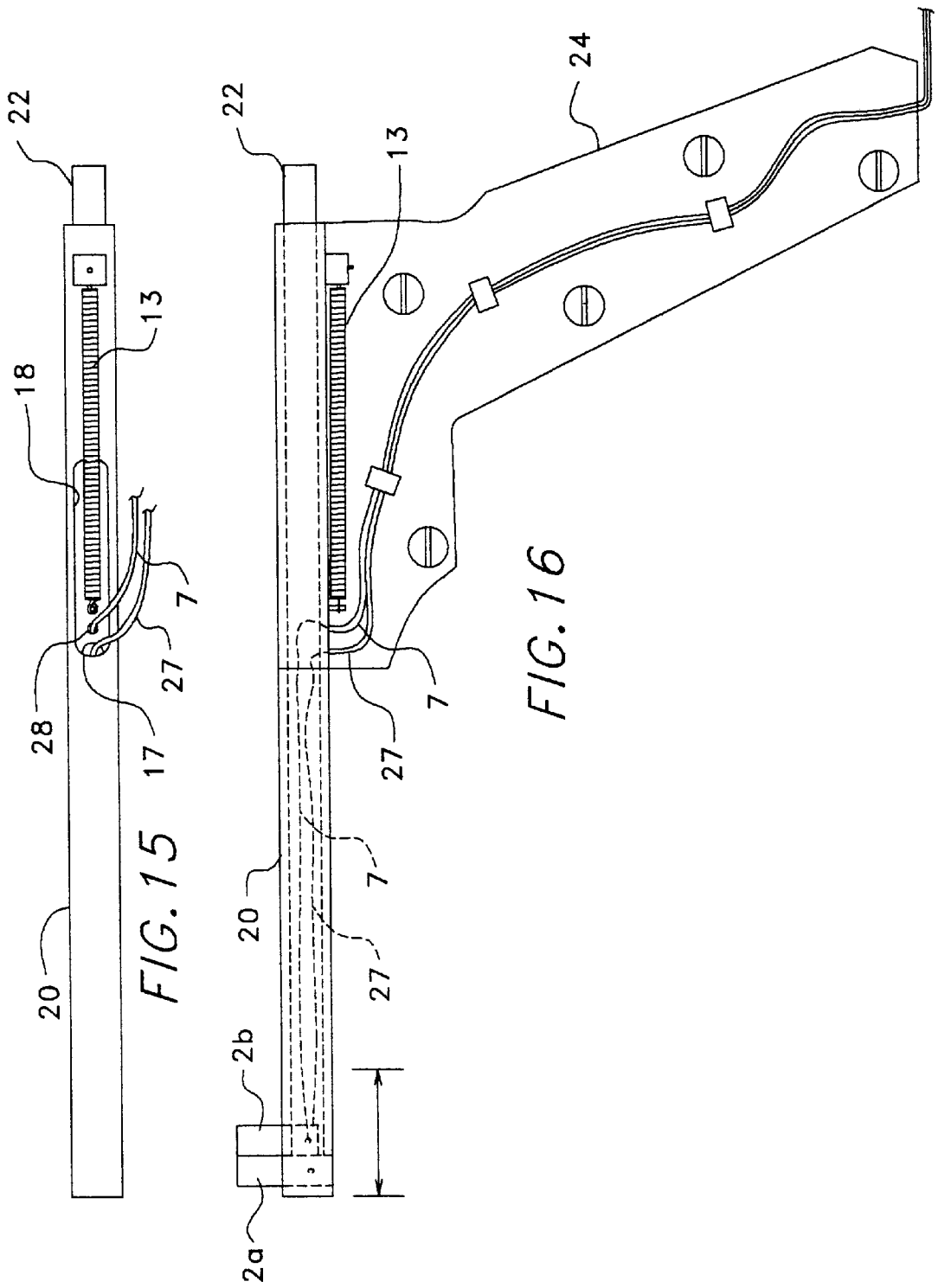

ELECTROSURGICAL DEVICE FOR UVULOPALATOPLASTY

RELATED APPLICATION

This application is a continuation of applicant's patent application Ser. No. 08/854,926 filed May 13, 1997, entitled ELECTROSURGICAL DEVICE FOR UVULOPALATOPLASTY U.S. Pat. No. 5,921,983.

FIELD OF THE INVENTION

The present invention relates to an electrosurgical instrument, and more specifically to a bipolar electrosurgical instrument designed for uvulopalatoplasty.

BACKGROUND OF THE INVENTION

Snoring, a problem which afflicts millions of people and their partners, occurs when there is obstruction of the free flow of air through the passages of the back of the mouth and nose. This is most often caused by excessive tissue in the uvula and soft palate. Snoring can be a sign of a more serious condition such as sleep apnea, and patients should be evaluated by a physician. Sleep apnea is caused by a combination of a floppy uvula and soft palate and the tongue falling back to shut off the postnasal space. Surgery to correct this involves removal of the excess soft palate and uvula with uvulopalatopharyngoplasty, which is a hospital-performed operation requiring general anesthesia and a hospital stay of up to three days.

Uvulopalatoplasty, however, can be performed in doctors' offices to relieve sleep apnea and reduce snoring. Currently in use in some large metropolitan areas is laser-assisted uvulopalatoplasty. However, laser equipment can be prohibitively expensive for some practitioners. Laser surgery systems range in cost from $40,000 to $150,000. Laser surgery is not the subject of this invention. For purposes of the present invention, electrosurgical devices are contemplated. Many doctor's offices are equipped with electrosurgery instruments. The present invention is designed to be adapted to operate in conjunction with such instruments. Exemplary of such instruments are those manufactured by ConMed, Aspen Surgical Systems, Englewood, Colo.

None of the prior art electrocautery devices appear to have been designed for uvulopalatoplasty, since they are too large and unwieldy to fit easily into a patient's mouth.

U.S. Pat. Nos. 4,936,842 and 4,823,791 to Frank D. Amelio describe electrosurgical instruments for removing hemorrhoids and anal warts. Amelio '791 describes a detachable barrel. The barrel portion or "probe"described in the '791 patent is a single barrel which contrasts to the opposing jaw members of the present invention. No "snipping" action can be achieved by the Amelio device. The device of the '842 Amelio patent shows a handle mechanism to hold the detachable barrel. An important distinction between the device of the present invention and the device described by Amelio '842 is the trigger mechanism described by Amelio compared to the thumb actuator of the present invention. The thumb actuator of the present invention is an important improvement over the trigger mechanism described by Amelio. The trigger of Amelio is actuated by pulling the index finger toward the handle. The present invention describes an actuating means which allows the index finger to be free to manipulate the entire device allowing greater control by the user than if the index finger was required to operate the trigger. A thumb actuator provides an additional advantage of not requiring additional space in front of the handle for an index finger actuator/trigger and its movement. Thus, the barrel of the present invention can be shorter than in devices having an index finger trigger. Another disadvantage of an index finger trigger design is the extra care required by the surgeon when positioning the instrument in the mouth to prevent premature actuation upon contact of the instrument with the patient's mouth. If this design is equipped with a "trigger guard" to prevent such premature actuation, even less manual control is afforded the surgeon due to the limited space between the patient's jaw and the patient's uvula and soft palate where the surgeon must position the cutting jaws of the instrument. The present invention overcomes this drawback by eliminating the trigger mechanism and replacing it with a thumb actuator means placed behind the barrel which affords the surgeon the maximum amount of maneuverability possible.

U.S. Pat. No. 5,445,638 to Rydell and O'Brien describes an instrument called bipolar coagulation and cutting forceps which has not only a trigger mechanism, but also a handle having finger guides which are squeezed together like a pair of scissors to operate the forceps. A device of this configuration would afford even less manual control to the surgeon.

SUMMARY OF THE PRESENT INVENTION

The present invention offers a greatly improved device for performing electrosurgical uvulopalatoplasty. The device of the present invention is dimensioned to fit easily into a patient's mouth, and affords the surgeon increased manual control over prior art devices. Manual control is increased in the present invention by a direct thumb actuating means which, when depressed by the thumb of the user, engages the barrel which closes the jaws of the cutting mechanism to simply "snip" the uvula and surrounding soft palate tissue, if desired.

The present invention is contemplated to include two configurations. The first configuration comprises a handle having an actuator means which actuates a barrel fixedly mounted to the handle. This embodiment is contemplated to be disposable for single patient use. The second configuration comprises a handle having an actuator means having a detachable barrel. The advantage of having a detachable barrel is ease and economy of sterilization. An interchangeable barrel also permits economic optimization of manufacturing costs since less material is used for the interchangeable barrel since the handle is reused. The detachable barrel comprises a hollow tube upon which is mounted a pair of jaws, each jaw of which is connected to a wire, so that when the jaws are closed, an electrical current is produced which cauterizes the tissue. The jaws are comprised of two jaw members which make electrical contact when they are in the closed position. One of the jaw members is fixed and the second jaw member is moved into position so as to make an electrical contact with the first jaw member when the thumb actuating means is engaged by the thumb of the user to engage the barrel to close the jaws.

BRIEF DESCRIPTION OF THE DRAWINGS

FIG. 13 is a bottom view of the barrel of the single-use unit embodiment of the present invention in the preactuation position.

FIG. 14 is a side view of the entire handle and barrel of the single use unit embodiment of the present invention in the preactuation position.

FIG. 15 is a bottom view of the barrel of the single-use unit embodiment of the present invention in the actuation position.

FIG. 16 is a side view of the entire handle and barrel of the single use embodiment of the present invention in the actuation position.

DETAILED DESCRIPTION OF THE INVENTION

The detachable barrel of the present invention is comprised of any hollow tubular member which is capable of having inserted therein a small diameter tube so that a "telescoping" effect can be achieved, thus creating an outer barrel and an inner barrel. The diameter of these hollow tubular members can be comprised of any geometric configuration, for example, round, square, or flexible, so that the inner tube can house the electrical wires connected to the electrical contact to plug into the receptacle in the handle.

Figure 1:
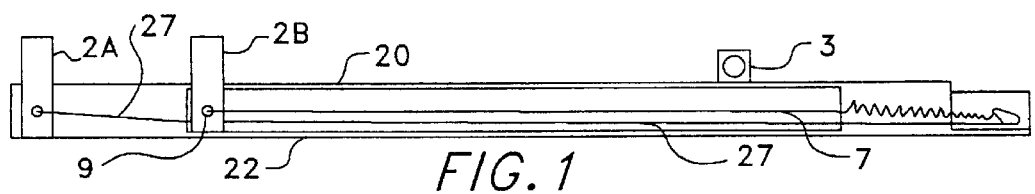
FIG. 1 is a side view of the detachable barrel in the open or pre-actuation position.
Figure 3:
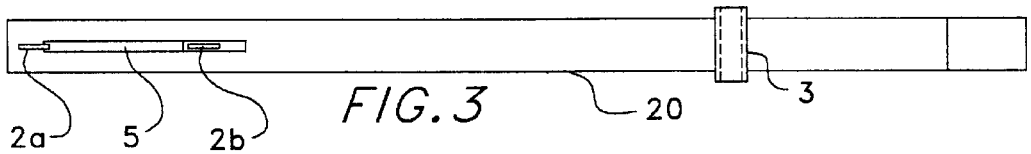
FIG. 3 is a top view of the detachable barrel in the open or pre-actuation position.
Figure 4:
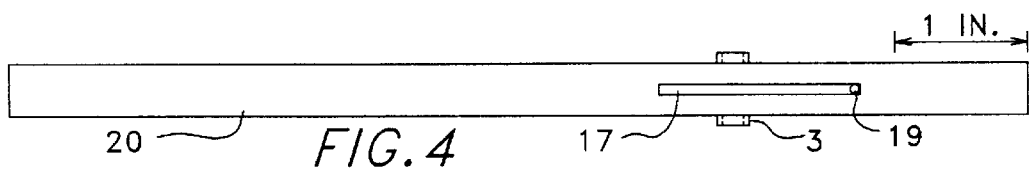
FIG. 4 is a bottom view of the detachable barrel in the open or pre-actuation position.
Figure 5:
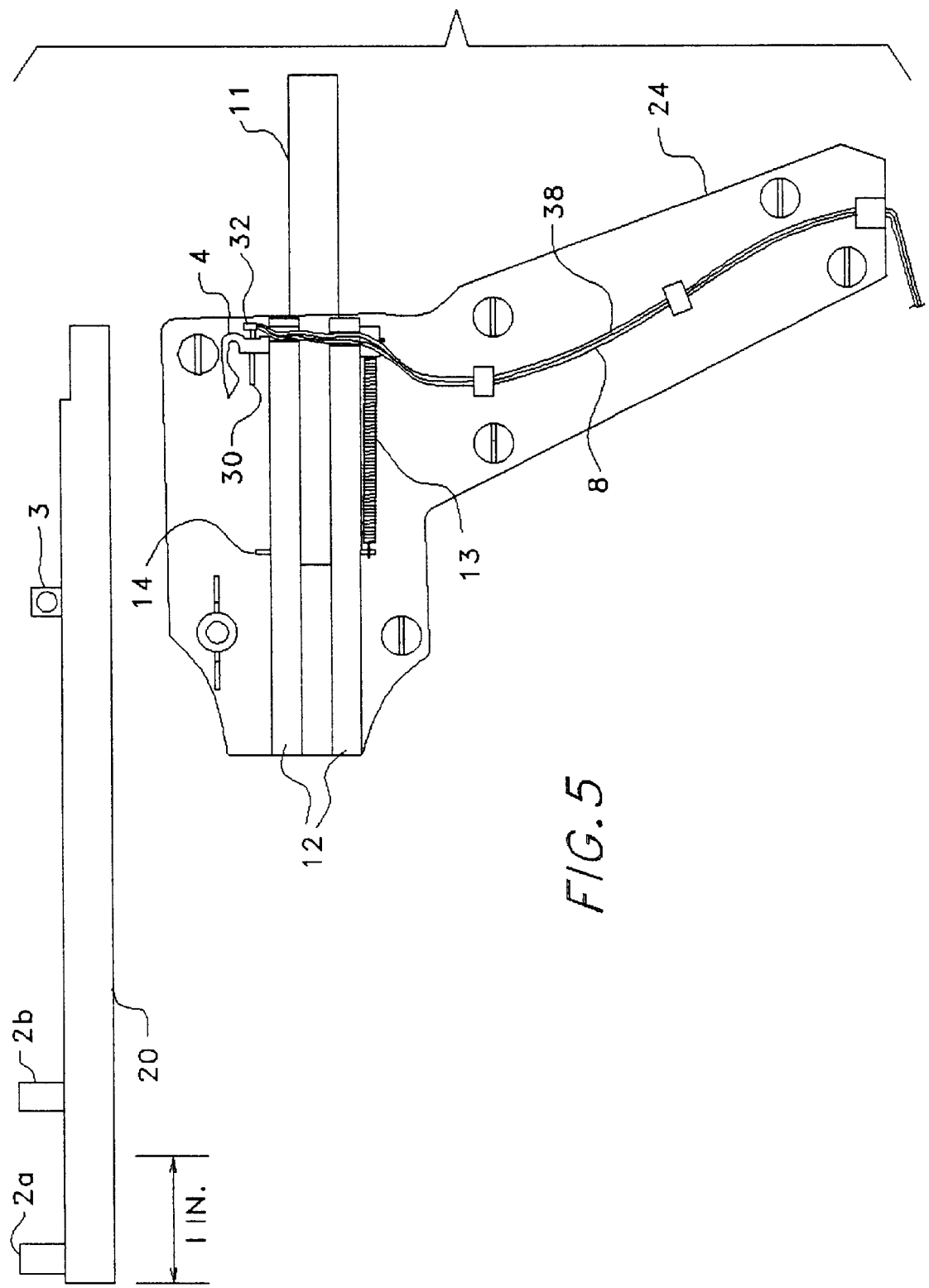
FIG. 5 is a side view of the handle.
Figure 9:
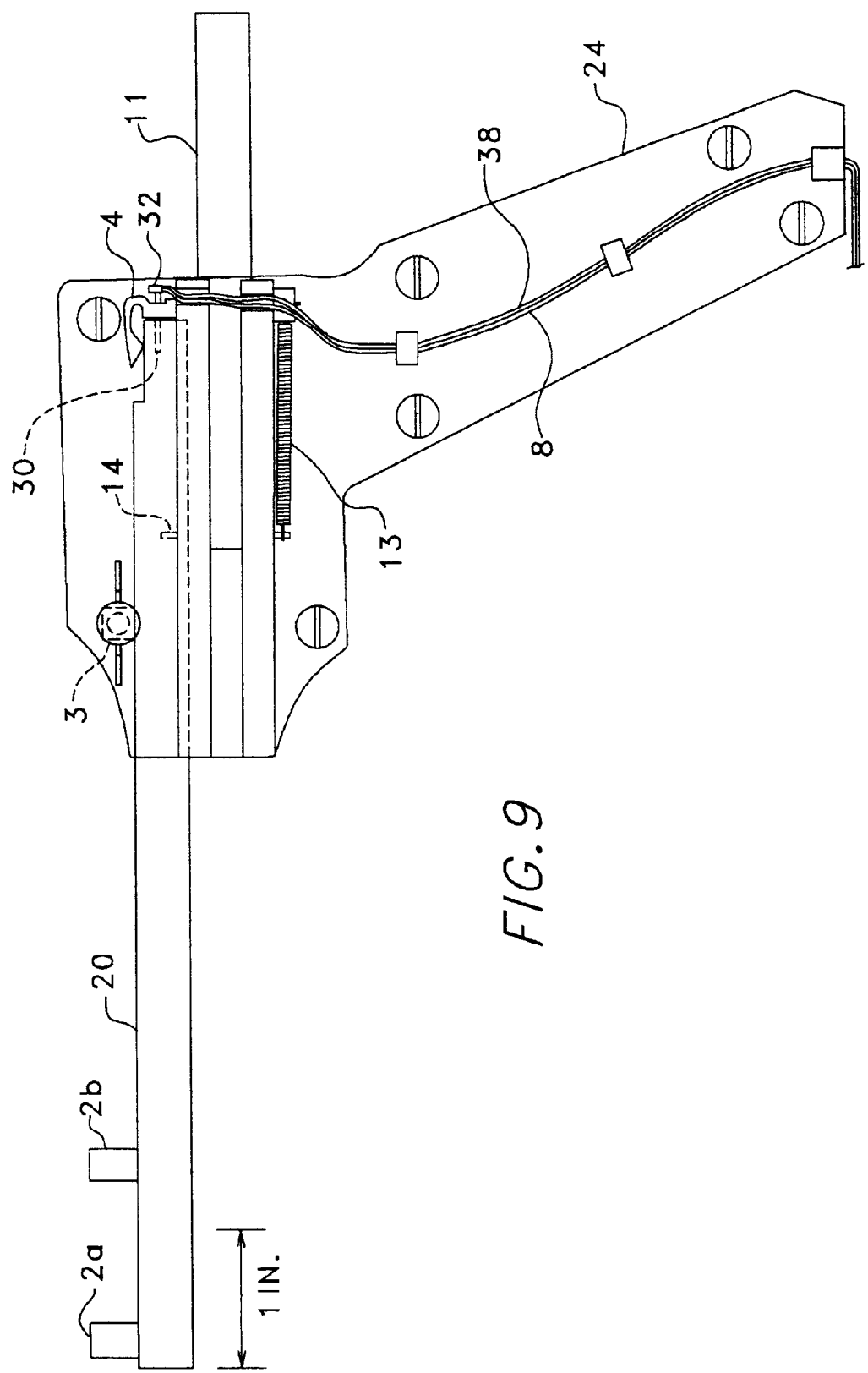
FIG. 9 shows the barrel mounted in the handle in a pre-actuation position.
Figure 10:
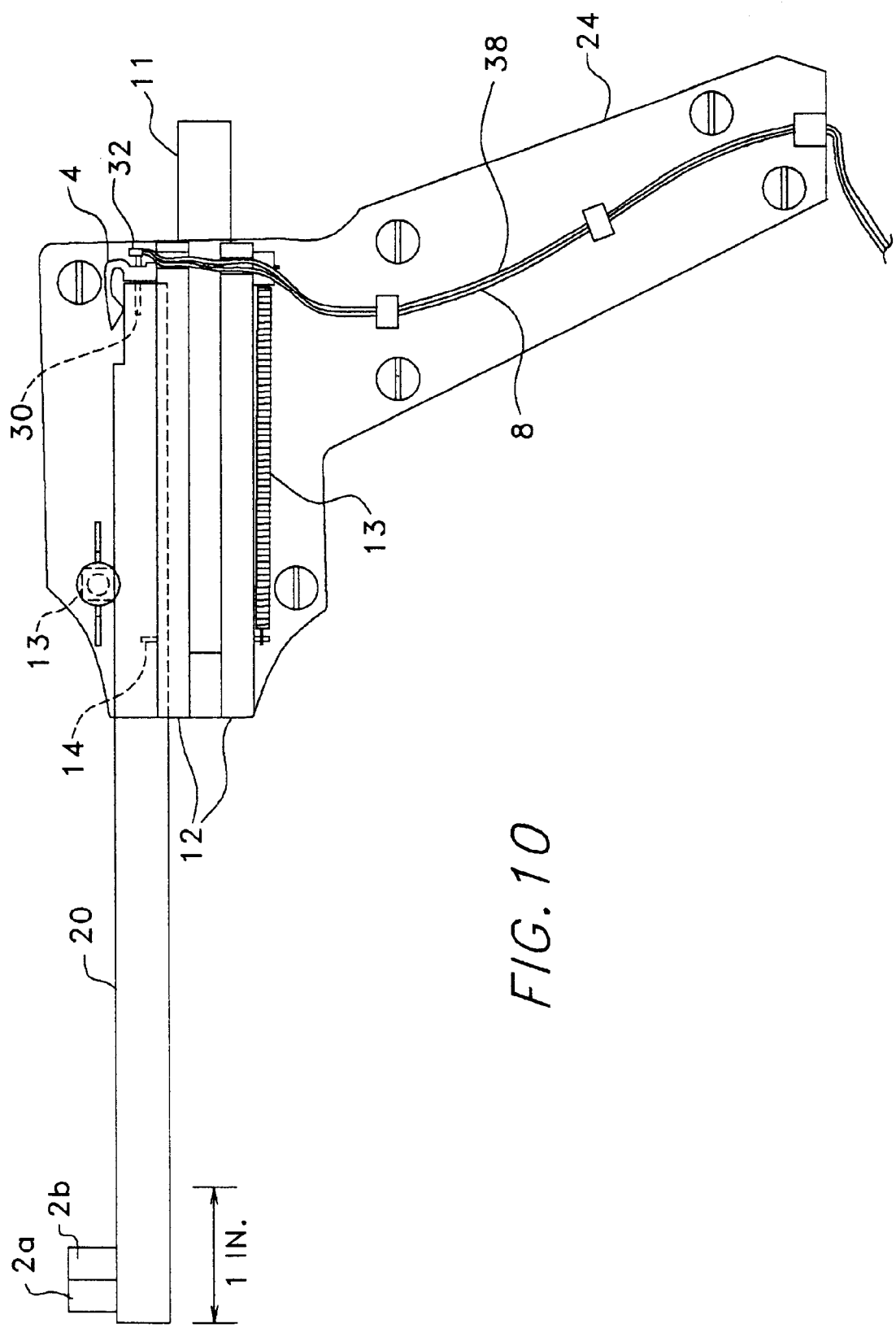
FIG. 10 shows the barrel mounted in the handle in an actuation position.
Figure 12:
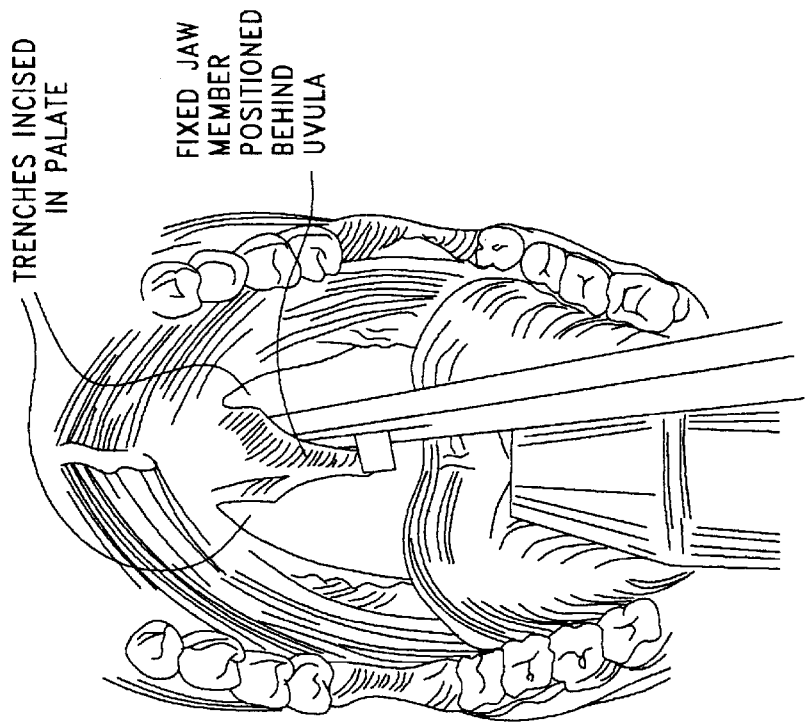
FIG. 12 is a figure showing the device of the present invention positioned for use behind the uvula in a human mouth.
Figure 11:
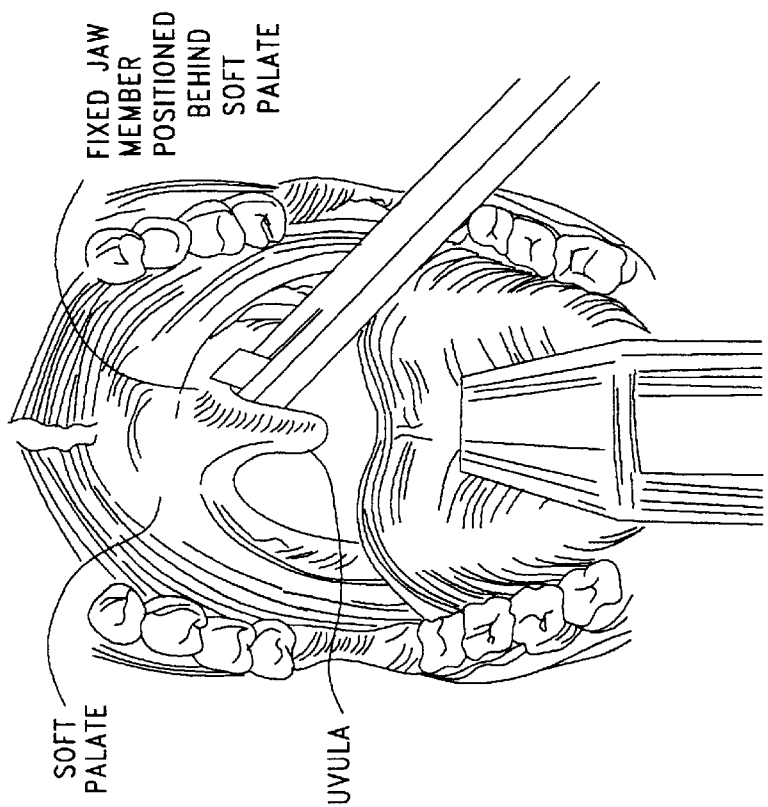
FIG. 11 is a figure showing the device of the present invention positioned for use behind the soft palate in a human mouth.

Turning more specifically to FIG. 1, The outer barrel 20 is equipped with one fixed jaw member 2a adjacent to an elongate top slot 5 (shown in FIG. 3). The outer barrel 20 holds the fixed jaw member 2a which is attached to wire 27 leading to the electrical contact 30 (shown in FIG. 5). Turning to FIGS. 4 and 5, the outer barrel 20 also has a bottom slot 17 in the bottom for accommodating the movement of projection 14 which fits into hole 20 in the inner barrel 22 as it slides within the outer barrel 20. Outer barrel 20 houses the inner barrel 22, which inner barrel 22 serves as the mount for the movable jaw member 2b which is connected to wire 27 at contact point 9 leading to the electrical contact 30 (shown in FIG. 5). The movable jaw member 2b is fixed on the surface of the inner barrel 22. Wire 7 is connected to electrical contact 30 with an amount of wire sufficient to span the distance from the contact point 9 on movable jaw member 2b to electrical contact 30 when the movable jaw member 2b is brought from the preactuation position to the actuation position which brings movable jaw member 2b into contact with fixed jaw member 2a. When the inner barrel 22 is in the preactuation position, the excess amount of wire 7 (i.e. equal to the distance between fixed jaw 2a and movable jaw 2b when at preactuation position) coils into the space between the end of the inner barrel and the electrical contact 30 which space must be sufficient to allow the excess wire to fold or store therein. As an alternative, to eliminate the need to have wire 7 coil in the space between the end of the inner barrel and the electrical connector, the movable jaw member 2a may be attached to the electrical contact with a sliding connector arrangement. In the present embodiment, when in the preactuation position, this excess amount of wire is held in place by the elastic force provided by the elastic force providing means 13 which returns the inner barrel to its original position. (See FIG. 5) The entire inner barrel moves when actuated, and since the inner barrel has jaw member 2b mounted to it, it is referred to by the term "movable jaw member." Jaw members 2a and 2b are comprised of metal having blades coated with a non-conducting coating on all surfaces except the cutting surface and attachments to the wires 7 and 27 leading to the electrical contact 30 (shown in FIG. 5). The cutting surfaces of the blades can be configured in a variety of geometries. Any geometry which allows a cut to be made, such as cutting edge of blades perpendicular to mounting of blades on barrel, or any angle between 90 degrees and about 30 degrees angled either forward or backward is contemplated. Geometries are also intended to include blade size or length as well as shape.

Each surgeon must determined which blade configuration optimizes precision for his or her use in performing the operation so as to remove only the amount of palate tissue necessary. Outer barrel 20 is mounted to the handle 24 by a non-permanent mounting means 3, as seen in FIG. 5. Any non-permanent mounting means such as a clip, thumbscrew, or the like is suitable for this purpose. When the outer barrel 20 is correctly positioned in the handle, it is in the open or preactuation position. The handle serves a means to hold the instrument, as well as a means to bring the actuating means into contact with the movable inner barrel. This movement of the inner barrel 22 is accomplished when the thumb of the user presses on the end of the actuating means 11 to move the inner barrel 22 so that the movable jaw member 2b is brought into contact with the fixed jaw member 2a. In the current embodiment, the actuating means 11 is in contact with the inner barrel 22 by means of a rod and hole mechanism. The rod 14 protrudes out of the actuating means through the bottom slot 17 of the outer barrel 20 and into the hole 19 of the inner barrel. It is intended that the cross-section of rod 14 can be any appropriate geometry. Although one may interpret the term "rod" to mean in this case an elongate protrusion having a circular cross-section, it is contemplated that any appropriate geometry, such as a square, triangle, hexagon or any other polygon for example, is suitable. When the actuating means 11 moves forward, so does the inner barrel 22, thereby bringing movable jaw member 2b into contact with fixed jaw member 2a. Actuating means 11 moves inside the handle 24 through guides 12 and is attached to the handle 24 by a means for providing an elastic force such as a spring or cable release mechanism 13 which serves to return the actuating means 11 to the open position after use. Elastic force providing means 13 is contemplated to be a spring for example, or any other mechanism which could return actuating means 11 to its preactuation position by providing an elastic force.

Figures 2A, 2B:
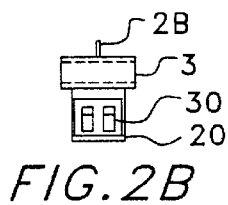
FIG. 2 is an end view of the detachable barrel, which end fits into the handle.

Electrical contact 30 in the outer barrel 20 plugs into electrical contact 32 in the handle. Electrical contact 32 is attached to wires 8 and 38 leading to the power supply. Although the drawings and description refer to the electrical contact 30 plugging into electrical contact 32, the reverse configuration is also possible, having electrical contact 32 plugging into electrical contact 30. This is shown in FIG. 2.

Also, the illustrative example describes the electrical supply requiring two wires. The present invention is also intended to include a system which would require an additional wire or wires, if desirable.

Referring specifically to FIG. 5, mounted on the top of guide 12 is a clip 4 which holds outer barrel 20 in the handle. This particular description includes clip 4 as a mounting means for holding the barrel 20 in the handle 24. However, any design which would allow this firmly held juxtaposition is contemplated, which includes mounting of the clip or mounting means on the top or side of guide 12, as well as the clip or mounting means being mounted on one or both sides of the handle. Along with clip 4, fastening means 3 which is part of outer barrel 20, securely fastens the barrel into the handle 24. Fastening means 3 can be a threaded hole and butterfly nut, for example. However, fastening means 3 can be any non-permanent fastening means such as a clip, spring, bayonet mount, or the like.

Figure 6:
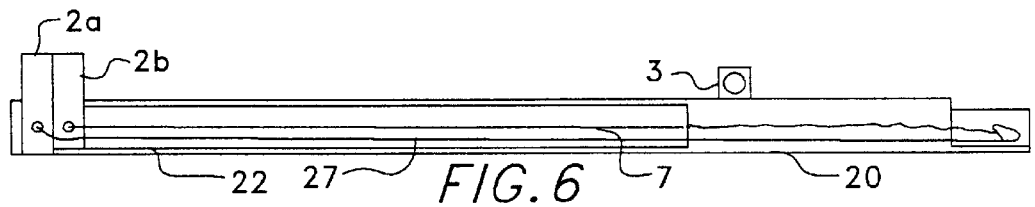
FIG. 6 is a side view of the detachable barrel in the closed or actuation position.
Figure 7:
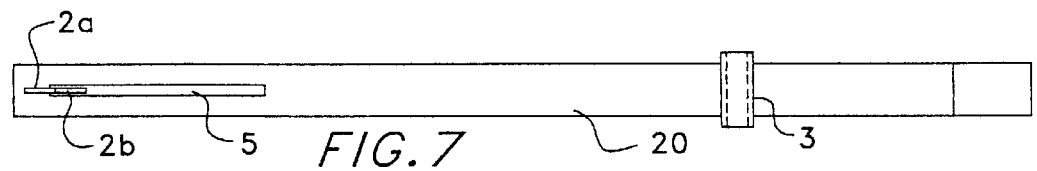
FIG. 7 is a top view of the detachable barrel in the closed or actuation position.
Figure 8:
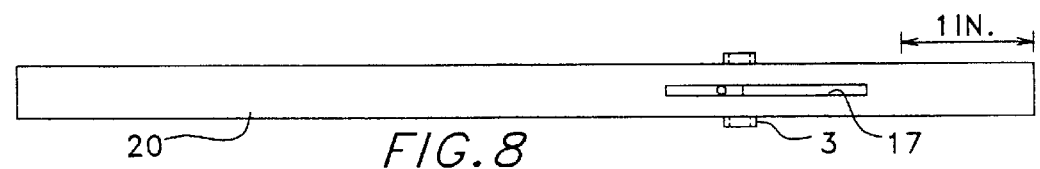
FIG. 8 is a bottom view of the detachable barrel in the closed or actuation position.

When actuating means 11 is pressed by the thumb of the user to the closed or actuation position, an electrical current passes between fixed jaw member 2a and movable jaw member 2b. This electrical current cauterizes the tissue between the two jaw members and "snips" off the tissue. As can be seen from FIGS. 6, 7, and 8, showing the detachable barrel 20 of the inventive device in the closed or actuation position, jaw members 2a and 2b are in contact with one another, and the rod 14 is moved forward in the bottom slot 17. This is an improvement over laser-assisted uvulopalatoplasty because the present invention cauterizes the tissue as it cuts, thus preventing excessive bleeding, which can occur during laser surgery. In addition, the present invention minimizes the risk of burning non-targeted tissue which also can occur during laser surgery.

Another preferred embodiment of the present invention comprises a handle with a permanently fixed barrel. This is a single-use unit envisioned to be disposable after each patient. This eliminates the need for sterilization, since the entire device can be manufactured as a sterile unit. FIG. 13 is a bottom view of the barrel of the single use unit embodiment of the present invention in the preactuation position. FIG. 14 is a side view of the entire handle and barrel of the single use unit embodiment of the present invention in the preactuation position. FIGS. 15 and 16 show this embodiment in the actuation position, respectively. Operation of this embodiment is similar to operation of the detachable barrel embodiment. The operation of the single-use embodiment is described below.

Turning more specifically to FIG. 14, the outer barrel 20 is equipped with one fixed jaw member 2a adjacent to an elongate top slot (shown in FIG. 3). The outer barrel 20 holds the fixed jaw member 2a which is attached to wire 27 leading to the electrical supply (not shown). Turning to FIG. 13, the outer barrel 20 also has an opening 18 in the bottom for accommodating the movement of wire 7 and the egress of wire 27 during the movement of the inner barrel 22 as it slides within the outer barrel 20. Outer barrel 20 houses the inner barrel 22, which inner barrel 22 serves as the mount for movable jaw member 2b which is connected to wire 7 leading to the electrical supply. Turning to FIG. 13, inner barrel 22 has a hole 28 in the bottom for the exit of wire 7. The bottom of inner barrel 22 also has an elongated slot 17 to accommodate the egress of wire 27. Hole 28 and slot 17 line up with opening 18 in outer barrel 20. As shown in FIG. 13, when in the preactuation position, the hole in inner barrel 22 is closest to the user. As shown in FIG. 15, when actuated, inner barrel 22 moves forward in outer barrel 20 and slot 17 and hole 28 are closest to the patient. The movable jaw member 2b is fixed on the surface of the inner barrel 22. The inner barrel 22 also serves as the actuating means. This single-use embodiment has no separate actuating means as is described for the interchangeable barrel version described above. Wire 7 is of sufficient length to span the distance from the contact point 9 on the movable jaw member 2b to the electrical supply when the movable jaw member 2b is brought from the preactuation position to the actuation position which brings movable jaw member 2b into contact with fixed jaw member 2a. Wire 7 is held taught at its egress point at hole 28 from inner barrel 22. When actuated, a portion of wire 27 (equal to the distance between fixed jaw member 2a and movable jaw member 2b) egresses through slot 17 in inner barrel 22 and through opening 18 in the outer barrel when the movable jaw member 2b is actuated and brought into contact with fixed jaw member 2a. Elastic force providing means 13 returns the inner barrel 22 to its preactuation position after use.

Various modifications and variations of the described invention will be apparent to those skilled in the art without departing from the scope and spirit of the invention. Although this invention has been described by referring to a specific preferred embodiment, it is to be understood that the invention as claimed should not be unduly limited to such a specific embodiment. Indeed, various modifications of the described mode for carrying out the invention which are obvious to those skilled in the art of electrosurgery or related fields are intended to be within the scope of the following claims.

What is claimed is:

1. An electrosurgical device comprising:

a handle;

an outer barrel having a slot formed therein;

mounting means for removably attaching said outer barrel to said handle;

an inner barrel slidable within said outer barrel between an open position and a closed position;

a fixed jaw connected to said outer barrel;

a moveable jaw connected to said inner barrel, said moveable jaw extending through said slot, said moveable jaw contacting said fixed jaw when said inner barrel is in said closed position; and electrical connections to said fixed jaw and to said moveable jaw for completing an electrical circuit through a patient's tissue between said fixed jaw and said moveable jaw.

2. The electrosurgical device of claim 1 further comprising a release mechanism to return said inner barrel to said open position.

3. The electrosurgical device of claim 2 further comprising a thumb-actuating means movable between a depressed position and a released position for sliding said inner barrel to said closed position when said actuating device is depressed, said release mechanism returning said actuating device to said released position when said actuating means is released.

4. The electrosurgical device of claim 1 wherein said fixed jaw and said moveable jaw comprises blades.

5. The electrosurgical device of claim 1 wherein said handle comprises a pistol grip.

6. An electrosurgical device comprising:

a handle;

an outer barrel removably attached to said handle;

an inner barrel slidable within said outer barrel between an open position and a closed position;

a fixed jaw connected to said outer barrel;

a moveable jaw connected to said inner barrel, said moveable jaw contacting said fixed jaw when said inner barrel is in said closed position;

an actuating device moveable within said handle between a depressed position and a released position, when said inner barrel sliding to said closed position when said actuating device is depressed;

a return mechanism providing an elastic force to return said actuating device to said released position and said inner barrel to said open position when said actuating device is released; and electrical connections to said fixed jaw and to said moveable jaw for completing an electrical circuit through a patient's tissue between said fixed jaw and said moveable jaw when said actuating device is in said depressed position.

7. The electrosurgical device of claim 6 wherein said handle further comprises electrical contacts, and wherein said outer barrel further comprises complementary electrical contacts engaging said handle electrical contacts for supplying electrical current to said fixed jaw and said moveable jaw.

8. The electrosurgical device of claim 6 wherein said handle comprises a pistol grip.

9. The electrosurgical device of claim 6 further comprising mounting means for removably attaching said outer barrel to said handle.

10. The electrosurgical device of claim 6 wherein said return mechanism comprises a spring.

11. The electrosurgical device of claim 6 wherein said fixed jaw and said moveable jaw comprise blades.

12. An electrosurgical device comprising:

a pistol grip handle having electrical contacts connected to an external electrosurgical power supply;

a disposable barrel assembly having
   (a) an outer barrel having a slot formed therein;
   (b) an inner barrel telescoping between an open position and a closed position within said outer barrel;
   (c) mounting means for detachably securing said barrel assembly to said handle;
   (d) a fixed blade connected to said outer barrel;
   (e) a moveable blade connected to said inner barrel, said moveable blade sliding through said slot when said inner barrel is telescoped between said open position and said closed position, said moveable blade contacting said fixed jaw when said inner barrel is in said closed position; and
   (f) electrical contacts for engaging said electrical contacts of said handle and delivering electrical current to said fixed jaw and to said moveable jaw;

an actuating device moveable relative to said handle between a depressed position and a released position, said inner barrel sliding to said closed position when said actuating device is depressed; and a return mechanism providing an elastic force to return said actuating device to said released position and said inner barrel to said open position when said actuating device is released.

13. An electrosurgical device comprising:

a handle;

an outer barrel having a slot formed therein, said outer barrel attached to said handle;

an inner barrel slidable within said outer barrel between an open position and a closed position;

a fixed jaw connected to said outer barrel;

a moveable jaw connected to said inner barrel, said moveable jaw extending through said slot, said moveable jaw contacting said fixed jaw when said inner barrel is in said closed position; and electrical connections to said fixed jaw and to said moveable jaw for completing an electrical circuit through a patient's tissue between said fixed jaw and said moveable jaw.

14. The electrosurgical device of claim 13 further comprising a release mechanism to return said inner barrel to said open position.

15. The electrosurgical device of claim 13 wherein said fixed jaw and said moveable jaw comprise blades.

16. The electrosurgical device of claim 13 wherein said handle comprises a pistol grip.

* * * * *